United States Patent [19]

Clark

[11] Patent Number: 4,683,090
[45] Date of Patent: Jul. 28, 1987

[54] PURIFICATION OF ORGANOSULFONYL HALIDES

[75] Inventor: Roger T. Clark, Pottstown, Pa.

[73] Assignee: Pennwalt Corporation, Philadelphia, Pa.

[21] Appl. No.: 436,494

[22] Filed: Oct. 25, 1982

[51] Int. Cl.$^4$ .......................................... C07C 143/70
[52] U.S. Cl. .............................................. 260/543 R
[58] Field of Search ...................... 260/543 R, 543 F

[56] References Cited

U.S. PATENT DOCUMENTS

| | | | |
|---|---|---|---|
| 2,276,097 | 3/1942 | Salzberg | 260/543 F |
| 2,884,369 | 4/1959 | Mattox et al. | 208/91 |
| 3,168,485 | 2/1965 | Knobloch et al. | 502/436 |
| 3,336,382 | 8/1967 | Pearson et al. | 260/543 F |

OTHER PUBLICATIONS

*Hackh's Chemical Dictionary*, 4th Ed. (1969), McGraw-Hill, Publ. at p. 424.
Roberts, John D. et al., *Basic Principles of Organic Chemistry*, (1965), W. A. Benjamin, Publ. pp. 1016–1018.
Kirk–Othmer, *Encyclopedia of Chemical Technology*, 2nd Ed., vol. 4, pp. 149–152.
Kirk–Othmer, *Encycl. of Chem. Tech.*, 3rd Ed., vol. 4, pp. 566–567, (1978).
Kirk–Othmer, *Encycl. of Chem. Tech.*, 3rd Ed., vol. 9, pp. 676 and 712, and vol. 11, p. 973, (1980).

*Primary Examiner*—Paul J. Killos
*Assistant Examiner*—L. Hendriksen

[57] ABSTRACT

Metallic impurities are removed from liquid organosulfonyl halides by passing the contaminated material through a bed of activated carbon, preferably activated carbon containing adsorbed water.

4 Claims, No Drawings

PURIFICATION OF ORGANOSULFONYL HALIDES

This invention relates to the purification of metal contaminated liquid organosulfonyl halides. More particularly, it relates to the removal of dissolved or suspended metal compounds, for example, iron and copper compounds, from such liquid halides by passage of the liquid through activated carbon.

BACKGROUND OF THE INVENTION

Because of their corrosive nature, organosulfonyl halides, as exemplified by alkane sulfonyl chlorides, easily become contaminated with metal salts and other metal compounds during preparation, handling and storage. Metal contamination, by discoloring the product and possibly catalyzing unwanted side reactions, such as hydrolysis, makes the product unsuitable for many industrial applications.

The literature describes the use of activated carbon for removing trace metals from waste water[1], but the metal is first chelated by a chelating agent such as 8-hydroxyquinoline and the chelate, in turn, is absorbed by the carbon. The prior art also discloses removal of organically combined metals from heavy gas oil feed stocks[2] at high temperature (300°–750° F.) by activated carbon. Further, the art shows the use of certain acidic organic compounds, such as phthalic acids for removing metal compounds, such as iron compounds, from activated carbon.[3]

[1] Analytical Chemistry, Vol. 49, 311 (1977)
[2] U.S. Pat. No. 2,884,369 (1959)
[3] U.S. Pat. No. 3,168,485 (1965)

STATEMENT OF THE INVENTION

This invention relates to the process of purification of a liquid organosulfonyl halide containing a metal compound contaminant by passing said liquid halide in contact with activated carbon whereby the amount of metal compound contaminant is reduced. A preferred embodiment of the process employs activated carbon having up to about 2.5 percent water, based on the weight of the carbon-water mass.

The following examples are illustrative and should not be construed as limiting the invention in any manner. Alkane sulfonyl chlorides, as shown in the examples are representative of the liquid organosulfonyl halides which can be purified using the procedure of this invention.

EXAMPLE 1

A 50 ml. glass burett, wrapped in a heating tape, was charged with 22 cm$^3$ of granular activated carbon (NA-CAR-600 sold by North American Carbon, Inc.) and the carbon was saturated with water. The excess water was blown off at 25° C. by injecting a stream of dry nitrogen through the carbon. The carbon contained greater than 0.1 but less than about 5 percent water based on the weight of the mass. A 100 ml. sample of discolored methane sulfonyl chloride (MSC) containing iron compounds [analyzed as 142 parts per million (ppm) of iron] was heated to 50° C. and poured through the burett column which was maintained at 50° C. The recovered MSC was water white and, when analyzed, was found to contain only 5.3 ppm iron. A total of 500 mls. of contaminated MSC was passed through the carbon bed and there was no evidence of iron in the effluent in concentrations greater than 5.3 ppm.

The above procedure was repeated using the identical activated carbon except that it had been dried at 185° C. for one hour to contain less than 0.1 percent water. The resulting MSC contained 14.5 ppm. iron.

The above procedure was repeated except that a dry cation exchange resin (Dowex A-1 sold by the Dow Chemical Company) replaced the activated carbon. The MSC, on analysis, showed the original 142 ppm of iron to be present.

The above procedure was again repeated except that the activated carbon was replaced with a dry silica gel (Grace Davidson-Grade 40). The effluent MSC was found to contain the original 142 ppm of iron.

EXAMPLE 2

The dried (>0.1% water) activated carbon containing burett was prepared as described in Example 1. A 100 ml. sample of discolored MSC containing suspended copper compounds (analyzed as 13 ppm copper) was heated to 50° C. and poured through the burett column which was also maintained at 50° C. The recovered MSC was water white and, when analyzed, was found to contain only 0.6 ppm copper.

The above procedure was repeated with 100 ml. of discolored butane sulfonyl chloride (BSC) contaminated with 3.7 ppm copper. The effluent BSC was water white and on analysis, was found to contain only 0.9 ppm copper.

The procedure was repeated with 100 ml. of discolored BSC containing 6.8 ppm iron. The effluent BSC was water white and, on analysis, was found to contain 2.7 ppm iron.

EXAMPLE 3

The dried (>0.1% water) activated carbon containing burett was prepared as described in Example 1. A 100 ml. sample of discolored octane sulfonyl chloride (OSC) containing 0.2 percent (2000 ppm) by weight of iron [determined by atomic absorption (AA)] was heated to 50° C. and poured through the burett column maintained at 50° C. The effluent OSC remained colored and was found to have 0.14 percent (1400 ppm) by weight of iron (determined by AA).

The above example demonstrates that the high amount of contaminant in the sample overloads the activated carbon bed used in the example. A larger bed would be required to remove additional amounts of metal contaminants from the organosulfonyl halides.

DISCUSSION OF THE INVENTION

The process of this invention provides inexpensive and effective removal of metal compound contaminants from liquid organosulfonyl halides by passing the liquid through a bed of activated carbon, preferably activated carbon containing a small proportion of water.

The liquid organosulfonyl halides which are treated in this process are those of the formula $RSO_2X$ wherein R is an alkyl, substituted alkyl, aryl or substituted aryl group and X is chloride or fluoride. Examples of these R groups are methyl, ethyl, propyl, isopropyl, butyl, octyl, dodecyl, octadecyl, hydroxyethyl, hydroxypropyl, phenyl and tolyl. Preferred organosulfonyl halides are the $C_1$ to $C_6$ alkyl sulfonyl chlorides.

An alkane sulfonyl chloride of particular commercial importance is methane sulfonyl chloride (MSC) and its purification treatment is an especially preferred embodiment of this invention. The purity of MSC is of importance because of its use in the preparation of, for example, dyestuffs and pharmaceuticals.

U.S. Pat. No. 4,035,242 describes a method for preparing MSC and recommends vacuum stripping of the crude product to produce a material having 99+% purity. Because of their lack of volatility, however, any metal contaminants would not be removed in the stripping procedure.

Metal compounds which are removed in this process are suspended or dissolved metal compounds. The metal compounds of particular concern are those of iron and copper.

The activated carbon which is used herein is a microcrystalline form of carbon which has been processed to provide internal porosity and is characterized by a large specific surface of 300–2500 square meters per gram. This carbon material may be prepared by properly treating any carbonaceous material of animal, plant or mineral origin including lignite, coal, bones, wood, peat and paper mill waste (lignin).

It is a preferred feature of this invention that the activated carbon contain some absorbed water. The water content preferably ranges from about 0.1 to about 2.5 percent based on the weight of the carbon-water mass. The presence of the water in the carbon provides unexpectedly better purification results but the role of the water is not understood. It is speculated that it may help retain the metal compounds in the carbon pores by a coordination effect.

The temperature of operation of the process is not critical within the freezing and vaporization temperature range of the particular liquid organosulfonyl halide being treated. A preferred temperature range is from −10° to 100° C. with 20° to 50° C. being most preferred for convenience and economy.

The method of this invention can be operated in a batch or continuous manner, the latter being preferred wherein a stream of the contaminated product is continuously passed through a bed of activated carbon and the stream switched to a column containing a fresh bed when the original bed is spent.

The removal of large amounts of metal compound contaminants by the process of this invention is unexpected especially in view of the known process of using acidic organic compounds, such as phthalic acid which is similar in acidity to the organosulfonyl halides, to remove metal compounds from activated carbon. The opposite result of metal compound removal from the liquid organosulfonyl halide by passage through activated carbon, is surprising.

I claim:

1. A method for the purification of a liquid organosulfonyl chloride, said liquid organosulfonyl chloride having the formula $RSO_2Cl$ wherein R is an alkyl group having from 1 to 6 carbon atoms and containing an inorganic compound of iron or copper as a contaminant, comprising passing said liquid organosulfonyl chloride through a bed of activated carbon whereby the amount of said contaminant in the liquid chloride is reduced.

2. The method of claim 1 wherein the activated carbon contains from about 0.1 to about 2.5 percent adsorbed water, based on the weight of the carbon-water mass.

3. The process of claim 1 wherein R is methyl.

4. The process of claim 2 wherein R is methyl.

* * * * *